(12) United States Patent
Mercer et al.

(10) Patent No.: US 9,446,198 B2
(45) Date of Patent: Sep. 20, 2016

(54) MEDICATED MODULE WITH LOCK RING

(75) Inventors: David Richard Mercer, Warwickshire (GB); Garen Kouyoumjian, Warwickshire (GB); Malcolm Stanley Boyd, Warwickshire (GB); Michael Bainton, Warwickshire (GB); John David Cross, Northhamptonshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 368 days.

(21) Appl. No.: 14/110,545

(22) PCT Filed: Apr. 19, 2012

(86) PCT No.: PCT/EP2012/057153
§ 371 (c)(1),
(2), (4) Date: Oct. 8, 2013

(87) PCT Pub. No.: WO2012/143436
PCT Pub. Date: Oct. 26, 2012

(65) Prior Publication Data
US 2014/0031760 A1 Jan. 30, 2014

(30) Foreign Application Priority Data
Apr. 21, 2011 (EP) .................................... 11163374

(51) Int. Cl.
*A61M 5/00* (2006.01)
*A61M 5/31* (2006.01)
(Continued)

(52) U.S. Cl.
CPC ......... *A61M 5/3129* (2013.01); *A61M 5/2448* (2013.01); *A61M 5/326* (2013.01);
(Continued)

(58) Field of Classification Search
CPC .. A61M 5/19; A61M 5/31533; A61M 5/326; A61M 5/2448; A61M 5/3294; A61M 5/3129; A61M 2005/37267; A61M 2005/2073; A61M 2005/208; A61M 2005/2451; A61M 2005/1787

USPC .......................................................... 604/191
See application file for complete search history.

(56) References Cited

U.S. PATENT DOCUMENTS

| | | | |
|---|---|---|---|
| 6,699,224 B2 | 3/2004 | Kirchhofer et al. | |
| 7,654,865 B2 | 2/2010 | Chazottes et al. | |
| 2013/0204186 A1* | 8/2013 | Moore | A61M 5/2448 604/111 |

FOREIGN PATENT DOCUMENTS

| | | | | |
|---|---|---|---|---|
| FR | 1256429 | 3/1961 | | |
| GB | WO 2011117287 A1 * | 9/2011 | .......... | A61M 5/2448 |

(Continued)

OTHER PUBLICATIONS

International Preliminary Report on Patentability for Int. App. No. PCT/EP2012/057153, mailed Oct. 31, 2013.

(Continued)

*Primary Examiner* — Theodore Stigell
*Assistant Examiner* — Tiffany Legette
(74) *Attorney, Agent, or Firm* — McDonnell Boehnen Hulbert & Berghoff LLP (57) ABSTRACT

A medicated module for an injection system to co-deliver at least two medicaments is disclosed where a primary delivery device containing a primary medicament accepts a medicated module containing a single dose of a secondary medicament and where both medicaments are delivered through a hollow needle. The medicated module is initially in a locked state until attached to a drug delivery where a locking plate is moved to a triggering state. The medicated module does not require the user to manually engage a reservoir containing the secondary medicament. Instead, a biasing member automatically activates the reservoir when the needle guard is retracted when the module is in the triggering state. The needle guard prevents accidental needle sticks before and after an injection, and locks after dose delivery.

25 Claims, 6 Drawing Sheets (51) Int. Cl.
*A61M 5/24* (2006.01)
*A61M 5/32* (2006.01)
A61M 5/315 (2006.01)
A61M 5/34 (2006.01)
A61M 5/178 (2006.01)
A61M 5/20 (2006.01)

(52) U.S. Cl.
CPC ......... *A61M 5/3294* (2013.01); *A61M 5/2466* (2013.01); *A61M 5/3146* (2013.01); *A61M 5/31533* (2013.01); *A61M 5/347* (2013.01); *A61M 2005/1787* (2013.01); *A61M 2005/2073* (2013.01); *A61M 2005/3247* (2013.01); *A61M 2005/3267* (2013.01); *A61M 2205/581* (2013.01); *A61M 2205/582* (2013.01); *A61M 2205/583* (2013.01); *A61M 2205/584* (2013.01)

(56) References Cited

FOREIGN PATENT DOCUMENTS

| JP | 2002-534229 | 10/2002 |
| JP | 2008-536278 | 9/2008 |
| WO | 2009/022132 | 2/2009 |
| WO | 2010/139671 | 12/2010 |
| WO | 2010/139672 | 12/2010 |

OTHER PUBLICATIONS

Japanese Office Action for JP Application No. 2014-505620, dated Feb. 2, 2016.

International Search Report and Written Opinion for Int. App. No. PCT/EP2012/057153, mailed Sep. 5, 2012.

* cited by examiner

MEDICATED MODULE WITH LOCK RING

CROSS REFERENCE TO RELATED APPLICATIONS

The present application is a U.S. National Phase Application pursuant to 35 U.S.C. §371 of International Application No. PCT/EP2012/057153 filed Apr. 19, 2012, which claims priority to European Patent Application No. 11163374.9 filed Apr. 21, 2011. The entire disclosure contents of these applications are herewith incorporated by reference into the present application.

FIELD OF THE INVENTION

This invention relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, our invention concerns a medicated module where the user does not have to manually select or set the module to dispense the second drug agent because activation of the needle guard automatically causes the reservoir of secondary medicament to engage with dispensing conduits. Our invention includes a locking plate to prevent premature activation of the medicated module.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. Our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Our invention also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

A number of medical and pharmaceutical drug delivery devices known in the art utilize the release of stored energy to drive some part of their mechanism during use. This energy may be stored in various forms including elastic (e.g. a spring), electrical, chemical, potential, pneumatic or hydraulic. In situations where this energy is captured/stored during the manufacturing or assembly process, rather than being provided by the user/patient as part of the use operation (such as winding a spring or pushing a lever), it is important that the energy is not accidentally released (triggered) until the desired moment, i.e., it is not prematurely released during transport or storage or similar such handling.

For some medical devices, accidental triggering prior to use may either compromise the operability of the device, or may even render it unusable. This may be of particularly importance for single-use devices. For devices containing medicament, and where accidental triggering has the potential to compromise the integrity of the primary pack of medicament, such events are likely to be particularly undesirable as they have the potential to result in a patient being exposed to a potentially non-sterile or even harmful, degraded form of the medicament.

Prior to use, the transit and storage of the medical device may present numerous scenarios in which the stored energy could be unintentionally discharged. Factors that may cause an accidental triggering event may include, but are not limited to; the application of static loads (stacking, crushing), dynamic loads (e.g. impact, vibration), pack and/or device inversion or temperature fluctuation.

Latches, locks and similar systems for preventing non-intentional actuation are known in the art (e.g. in the field of fire-arms, auto injectors, etc.). Generally, such features either need to be designed to be intuitive or, more ideally, the system designed in such a way that the shift in state from "locked out" to "triggerable" happens automatically as part of the standard, correct use procedure. Our invention provides such an automatic shift in state that prevents accidental triggering prior to use. Our invention is applicable to any device where energy may be stored in the device prior to delivery to the user, particularly single-use or medicated devices where accidental triggering may render the device unusable. Examples of such devices are auto-injectors, safety needles, safety syringes, needle-free/jet injectors and pressurized medicament cartridges (such as those used in pMDIs).

These and other advantages will become evident from the following more detailed description of the invention.

SUMMARY

Our invention allows complex combinations of multiple drug compounds within a single drug delivery system. The invention allows the user to set and dispense a multi-drug compound device though one single dose setting mechanism and a single dispense interface. This single dose setter controls the mechanism of the device such that a predefined combination of the individual drug compounds is delivered when a single dose of one of the medicaments is set and dispensed through the single dispense interface.

By defining the therapeutic relationship between the individual drug compounds our delivery device would help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect this invention is of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one possible medicated module design, a bypass cavity or housing that surrounds the primary pack of medicament, preferably a single dose, is held in an initial priming mode position by stand-offs on the outer body housing of the module. Rotation of the bypass housing brings the stand-offs into line with pockets in the outer body, allowing the bypass housing to move axially in relation to the outer body and therefore engage the primary pack. Alternatively, the stand-offs can be positioned on the outer body and the pockets on the bypass housing. The present invention disclosed prevents accidental triggering by preventing rotation of the bypass housing relative to the outer body housing an axially sliding locking plate. The plate moves from an initial "locked" state to a "triggerable" state through attachment and interaction with the cartridge holder on the primary device. In the locked state the plate constrains the bypass housing to the upper hub in the outer body housing, preventing triggering. In the second "triggerable" position the plate has been moved axially (through attachment of the medicated module to the cartridge holder) and is no longer locked to the outer body, thereby allowing rotation and firing of the bypass housing at the appropriate time (as the user starts to retract the needle guard for injection and dispense).

The mechanism of our invention is automatically activated upon attachment of the medicated module to the primary device, which should typically occur only immediately prior to use. No additional use steps by the user are required to activate the module above what is now considered the current "state of the art" for the use of standard needles with existing injection devices.

In one embodiment of our invention there is provided a medicated module attachable to a drug delivery device that comprises an outer housing having an inner surface, a proximal end and a distal end, where the proximal end has an upper hub holding a first double-ended needle cannula and a connector configured for attachment to a drug delivery device. A bypass housing is located inside the outer housing that is configured to move both rotationally and axially in the proximal direction when the module is triggered during use. A locking plate is positioned between the proximal end of the bypass housing and the distal end of the upper hub. The upper hub has one or more cutouts that expose one or more engagement ramps on the proximal or upper side of the locking plate. These engagement ramps act as bearing surfaces when they come into contact with radially extending tabs on the distal end of a cartridge holder. Preferably the cartridge holder connection mechanism involves a rotation motion such that the tabs push down and ride along the locking plate engagement ramps.

There is a reservoir within the bypass housing, preferably comprising a single dose of a medicament. The medicated module assembly of our invention contains a needle guard that can reduce the risk of accidental needle sticks before and after use, reduce the anxiety of users suffering from needle phobia as well as preventing a user from using the device a subsequent time when the additional medicament has already been expelled. There is a also a biasing member engaged between the guard and a lower hub located at the distal end of the bypass housing.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be from about 3 to about 4 mm. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the needle guard or shield is configured to move axially in both the distal and proximal directions when pressed against and removed from an injection site. When the needle assembly is removed or withdrawn from the patient, the guard is returned to post-use extended position. A locking mechanism can be used to securely lock the guard from further substantial axial movement at the completion of the injection. A locking mechanism could also be used to further lock the medicated module from any further use and prevent the needle(s) from being reused. Likewise, there can be an additional locking mechanism that prevents the reservoir from being able to substantially move within the system even if the guard is held in an axially locked condition. By "substantial" movement we do not mean the typical amount of "play" in a system, but instead we mean that the guard and/or distal needle do not move axially a distance that exposes the distal end of the cannula once it is locked out.

Manually operated devices are sometimes not as intuitive as they could be and raise the risk of accidental misuse. Our invention solves this problem by utilizing a rotating cylinder that is moved by the retraction of needle guard thus activating the state change from prime dose to combination dose. The mechanism aims to make this actuation imperceptible to the user, consequently making the user experience of the module very similar to that of a standard commercially available and accepted needle or safety needle (i.e. unpack module, attach to a drug delivery device, prime drug delivery device, inject a set dose along with single dose in the module). In this way, the module mechanism aims to reduce the risk of unintentional misuse and to improve usability by replicating an already accepted practice for similar injection methods. However, such automatically triggering devices risk being triggered prematurely.

Another goal of our invention is to prevent premature triggering of the medicated module prior to use. Because the medicated module is designed to eliminate the need to have the user manually operate the medicated module to change the state of the module from a priming state to a combination dose delivery state there is a risk that the automatic triggering system might be accidentally triggered during shipment, storage, or mishandling of the device. To avoid this problem, a locking plate is included that prevents rotation of the bypass housing and thus the engagement of the needle cannulae with the reservoir. The locking plate remains in this first locked position until the medicated module is attached to a primary drug delivery device.

When the primary drug delivery device is attached to the upper hub of the module, the axially extending tabs on the cartridge holder connection means protrude through the cutouts in the upper hub and engage the ramps on the upper surface of the locking plate. As the cartridge holder connection means is pushed distally and rotated into the upper hub, the tabs engage the ramps and push the locking plate down in an axial direction disengaging the hub contact face from the cutout in the upper hub. This places the locking plate in its triggering position.

When the user pushes the needle guard against an injection site, the guard moves proximally relative to the outer housing. A biasing element is placed between the inside surface of the guard and the distal side of the lower hub. Preferably, the biasing element is a compression spring that preferably is in a pre-compressed state. Movement of the guard further compresses the biasing element exerting a force in the proximal direction on the lower hub and the bypass housing urging them both to move proximally. Movement of the guard also triggers the bypass housing to rotate. Because the locking plate is in the triggering position, the bypass housing rotates and then moves axially in the proximal direction moving the reservoir along with the bypass housing and causing the needle cannula in the upper and lower hubs to become fluidly engage with the medicament in the reservoir.

As the module mechanism does not require the user to access external features on the module for the purposes of actuation, the number of components and subsequent module size can be reduced/optimized. These factors make the mechanism ideal for a single-use, high-volume manufacture, and disposable device application. Alternatively, as the actuation is driven by a single action, the system lends itself to a resettable actuation mechanism. The preferred embodiment described below is the single use (non-resettable) version. The rotating bypass housing and lower hub in combination with a biasing force, preferably from a compression spring, causes theses parts to rotate and then to move axially as the needle guard is retracted. The needle guard is restrained rotationally with regard to the outer housing, but is free to move axially, between defined constraints, within the outer housing.

The user pressing the distal face of the needle guard against the skin causes axial motion of the needle guard in the proximal direction. This axial motion of the guard causes a rotation of the bypass housing, preferably through the engagement and action of an inward-facing drive tooth on the guard as it travels in a drive track having a non-linear path, which is located on the outer surface of the bypass housing. The lower hub, which preferably contains a double-ended needle cannula, also rotates and moves axially as the bypass housing rotates. It is this axial movement of the lower hub that results in the double ended needles located in the upper hub and the lower hub piercing the reservoir seals, moving it from a state of priming to combination dose delivery.

Further axial and proximal movement of the needle guard is required in order to pierce the skin, which compresses the biasing member creating a force that acts on the lower hub to result in the axial movement of the reservoir in the proximal direction. In normal use, once the drug has been dispensed and the needle is removed from the skin, the needle guard is allowed to return axially in the distal direction under the relaxation of the biasing member as it releases its stored energy. At some point along its return travel, a lock out mechanism is triggered locking out the needle guard from further use or exposing the needle. Should the user remove the device from the skin without dispensing fluid, but after the "commit" point has been passed, the needle guard would return to an extended position and lock out as previously described.

The medicated module assembly as described herein is attachable to a drug delivery device, preferably a pen shaped injection device, through an upper hub holding a first double-ended needle cannula and a connector configured for attachment to a drug delivery device. The hub can be a separate part from the housing or integral, for example molded as part of the housing. The connector can be any connector design, such as threads, snap fits, bayonet, luer lock, or combination of these designs.

Preferably, two needle cannula are used, a distal cannula and a proximal cannula, with both cannulae preferably being doubled-ended for piercing a septum or seal and for piercing skin. The distal needle is mounted in a lower hub and the proximal needle is mounted in the upper hub of the outer housing, each using any technique known to those skilled in the art, such as welding, gluing, friction fit, over-molding and the like. The medicated module assembly also contains a biasing member, preferably a compression spring. The biasing member is preferably in a pre-compressed state and positioned between the proximal inner face of the needle guard and the distal face of the lower hub. Although a preferred biasing member is a spring, any type of member that produces a biasing force will work.

The medicated module assembly of our invention automatically, once triggered, changes state from (1) a pre-use or priming state, where a small amount of primary medicament flows in a bypass around the reservoir containing a single dose of the secondary medicament, to (2) a ready-to-use or combination dose state, where both the upper and lower cannulae are in fluidic engagement with the fixed dose of the second medicament within the module and where a set dose of the primary medicament can be injected along with the non-settable single dose of secondary medicament in the reservoir, and finally to (3) a locked out state, where the needle guard is prevented from substantial proximal movement. The outer housing preferably has a window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both a pre-use priming position and a locked position of the guard after the medicated module assembly has been used to perform an injection.

Inside the bypass housing there is a cavity that contains the reservoir or capsule, which preferably comprises the single dose of medicament. As the needle guard is retracted during an injection, the reservoir is moved proximally with the bypass housing causing the seals of the reservoir to be pierced at its top and bottom by the needle cannula such that the medicament can be expelled from the reservoir during dose delivery. When connected to a drug delivery device containing a first medicament and prior to piercing the seals of the reservoir, the needle cannulae are only in fluid communication with the first medicament and a fluid flow path that bypasses the capsule. Preferably, a channel on the outside of the reservoir or alternatively on the inside surface of the bypass housing is part of this fluid flow path and is used in the priming function of the drug delivery device.

A further aspect of the invention relates to a method of dispensing a fixed dose of one medicament and a variable dose of a primary medicament from separate reservoirs that involves the steps of first attaching a medicated module to a delivery device set in a pre-use or prime only state. Attaching the module to the primary device moves the locking plate from the first locked state to a triggering state. When in the locked state the needle guard cannot move and rotate the bypass housing to engage the two needle cannula into the reservoir because the locking plate is rotatably fixed to the upper hub that is part of the bypass housing. The user can prime the dose delivery device using only the primary medicament and bypassing the second medicament. After priming the user begins the injection and the needle guard begins to retract and the module automatically changes to a second state that allows a combination delivery of the two medicaments. Upon completion of the delivery procedure and retraction of the needle from the injection site, the extension of the needle guard automatically changes the module to a third state.

During dispense, substantially the entire amount of second medicament has been expelled as well as the selected or dialed dose of the first medicament, through the single dispense interface. The reservoir preferably contains a flow distributor to ensure that substantially all the single dose of secondary medicament is forced out of the capsule by the primary medicament during an injection. The flow distributor can be a separate stand-alone insert or pin. Alternatively the flow distributor and the capsule together can be manufactured or assembled as a one-piece component where the flow distributor is integral with the reservoir or capsule.

Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). Further preferred materials include those that are typically used to manufacture septa or pistons (bungs) found in multi-dose medicament cartridges, however, any other material that is compatible with the drug could be used, e.g., glass, plastics or specific polymers, for example, TPE (thermo plastic elastomer); LSR (liquid silicone rubber); LDPE (low density polyethylene); and/or any kind of medical grade rubber, natural or synthetic.

By "substantially all" we mean that at least about 80% of the second medicament is expelled from the drug delivery device, preferably at least about 90% is expelled. In the third state, preferably the module is locked so as to prevent a second delivery or insertion by means of a locking mechanism.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module of the invention can be designed for use with any drug delivery device with an appropriate compatible interface. However, it may be preferable to design the module in such a way as to limit its use to one exclusive primary drug delivery device (or family of devices) through employment of dedicated/coded/exclusive features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of the invention, the primary drug delivery device is used more than once and therefore is multi-use; however, the drug delivery device may also be a single use disposable device. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the patient attempt to reuse a previously used medicated module, our invention includes the locking needle guard that is activated after a first predefined travel/retraction of the guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature of our invention is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Our invention also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

In one embodiment of our invention, a medicated module comprises an outer housing including an upper hub having a first needle configured for attachment to a drug deliver device. Inside the outer housing is a bypass housing adapted to rotate and move proximally relative to the outer housing, the bypass housing including a reservoir containing a medicament. A locking plate is slidably coupled to the bypass housing and movable between a locked state prior to attachment of a drug delivery device to the upper hub and a triggerable state after attachment of a drug delivery device to the upper hub. When in the locked state, the locking plate engages the upper hub and prevents the bypass housing from rotating relative to the upper hub. When in the triggerable state, the locking plate disengages the upper hub and the bypass housing is rotatable from a first angular position to a second angular position relative to the outer housing. When in the second angular position, the bypass housing translates axially relative to the outer housing and the reservoir is in fluid communication with the first needle.

In a preferred embodiment, the medicated module bypass housing may comprise a lower hub with a second needle. The second needle may be located at the distal end of the bypass housing.

In a further embodiment, the medicated module may comprise a needle guard coupled to the outer housing free to move axially, between defined constraints, within the outer housing and restrained rotationally with regard to the outer housing. In an extended position, the needle guard may cover the second needle.

The needle guard may be configured to cause the bypass housing being rotated when the needle guard is moved axially. Rotation may transfer the bypass housing from a first angular position to a second angular position, where the bypass housing is free to move axially. In a preferred embodiment, a biasing member may cause the bypass housing to be moved axially when in the second angular position.

The locking plate of the medicated module according to the invention may have a proximally projecting bearing surface exposed through the cutout.

The locking plate may have a radially projecting bypass housing locking slot configured to engage with ribs such that the locking plate is rotationally fixed to the bypass housing.

The locking plate may have axial detent tabs configured to engage with detent engagement faces on the bypass housing to prevent distal movement of the locking plate. Alternatively, the locking plate may be engaged to the bypass housing through snap fasteners to prevent distal movement of the locking plate.

The locking plate may have an outer housing contact face. In a first locked position or first position, the outer housing contact face may be engaged with the upper hub to prevent rotation of the bypass housing. In a second unlocked position or second position, the outer housing contact face may be disengaged from the upper hub to allow the bypass housing to rotate and move proximally.

The biasing member of the medicated module may be spring. According to an embodiment, the spring may be compressed and exerting a force on the lower hub (53) and the bypass housing (52).

The reservoir of the medicated module may be a single molded component having an internal cavity with an integral flow distributor. The reservoir may contain a liquid medicament. The medicament in the reservoir may comprises a GLP-1, in a preferred embodiment, the medicament in the reservoir may comprise a premix of insulin and a GLP-1.

The locking plate of the medicated module according to the invention may have a first position or locked state, where the locking plate constrains the bypass housing to the upper hub of the outer body. The locking plate may have a second position or triggerable state, wherein the locking plate has been moved axially and is no longer locked to the outer body thereby allowing rotation of the bypass housing.

The locking plate may be in the second position or triggerable state when the medicated module is attached to a drug delivery device.

Another aspect of the invention relates to a drug delivery device configured to be attached to a medicated module according to the invention. The drug delivery device may comprise at least one projection configured to engage the locking plate through the cutout of the medicated module according to the invention. The drug delivery device further may comprise a reservoir of primary medicament. The reservoir may be a cartridge or ampoule sealed with a septum at one end and having a piston at the opposite end. The drug delivery device further may a dose button configured to discharge the medicament from the reservoir. The drug delivery device may further comprise a dose setting member, e.g. dose dial sleeve. In a preferred embodiment the dose button is operably connected to a spindle that engages the piston in the primary reservoir. In a further embodiment the spindle is a rotatable piston rod comprising two distinct threads. When the drug delivery device is attached the septum of the reservoir is pierced by a needle, e.g. a double ended needle cannula. The needle may be part of the medicated module, e.g. the upper hub of the medicated module may contain the needle. Alternatively, the needle may be part of the drug delivery device, e.g. an injection needle attached to the distal end of the drug delivery device.

In one embodiment, the drug delivery device comprises a reservoir within a cartridge holder, wherein the cartridge holder comprises at least one projection, e.g. axially extending tabs on a cartridge holder, configured to engage the locking plate through the cutout of the medicated module according to the invention.

Another aspect of the invention relates to a system to deliver two or more medicaments operable through a single dispense interface, comprising a drug delivery device and a medicated module according to the invention. The drug delivery device may comprise a primary reservoir of medicament containing at least one drug agent and a dose button operably connected to the primary reservoir of medicament. When the medicated module is attached to the drug delivery device fluid communication is made between the medicament in the primary reservoir and the first needle.

When the medicated module is attached to the drug delivery device the locking plate may be disengaged from the upper hub and axial movement of the needle guard may compress the biasing member exerting a force in the proximal direction on the lower hub and the bypass housing urging them both to move proximally, causing the needle cannula in the upper and lower hubs to become fluidly engaged with the medicament in the reservoir.

In one embodiment of the drug delivery system, the drug delivery device (7) comprises at least one projection (49) configured to engage the locking plate (24) through the cutout (16). When the drug delivery device is attached to the medicated module, the at least one projection of the drug delivery device engages with a bearing surface of the locking plate causing the locking plate to be axially disengaged from the bypass housing and to be moved axially in distal direction allowing the locking plate to rotate relative to the upper hub.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
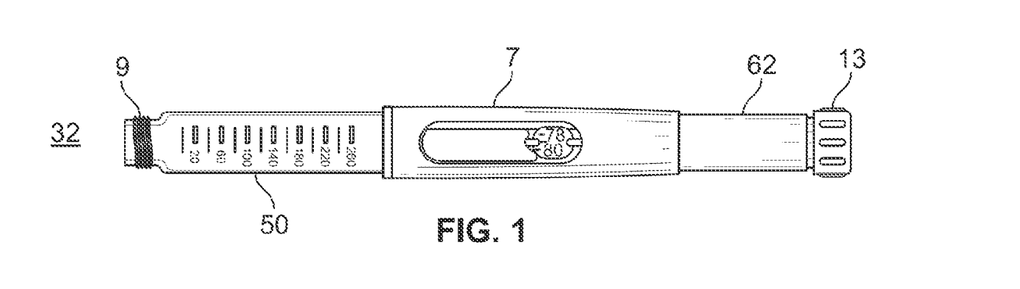
FIG. 1 illustrates one possible drug delivery device that can be used with the present invention.

The present invention administers a fixed predetermined dose of a secondary drug compound (medicament) and a variable dose of a primary or first drug compound through a single output or drug dispense interface. Setting the dose of the primary medicament by the user automatically determines the fixed dose of the second medicament, which preferably is a single dose contained in a capsule or reservoir having an integral flow distributor. In a preferred embodiment the drug dispense interface is a needle cannula (hollow needle). FIG. 1 illustrates one example of a drug delivery device 7 that the medicated module 4 (see FIG. 2 or 5) of our invention can be attached to the connection means 9 on cartridge holder 50 of distal end 32. Each medicated module is preferably self-contained and provided as a sealed and sterile disposable module that has an attachment means 8 compatible to the attachment means 9 at the distal end 32 of device 7. Although not shown, the medicated module could be supplied by a manufacturer in a protective and sterile container, where the user would peel or rip open a seal or the container itself to gain access to the sterile medicated module. In some instances it might be desirable to provide two or more seals for each end of the medicated module.

Figure 2:
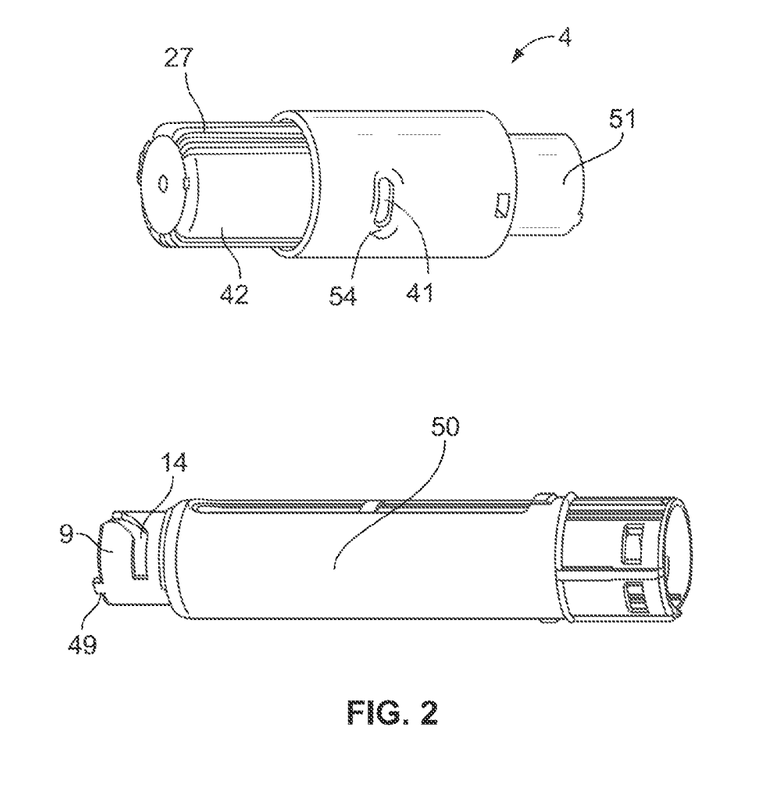
FIG. 2 illustrates an embodiment of the medicated module of the present invention, where the medicated module is separated from an attachable cartridge holder of the drug delivery device of FIG. 1.

Any known attachment means 8 can be used to attach the medicated module to the chosen drug delivery device, including all types of permanent and removable connection means, such as threads, snap locks, snap fits, luer locks, bayonet, snap rings, keyed slots, and combinations of such connections. FIG. 1 illustrates the attachment means 9 as threaded connection and FIG. 2 shows an alternate unique connection that is keyed specifically to a corresponding connection on medicated module 4, respectively. More specifically, the attachment means includes an axially extending cartridge holder tab 49 that, as explained in detail below, engages the locking plate 24 in the medicate module 4 through cutout 16 of upper hub 51.

Figure 5:
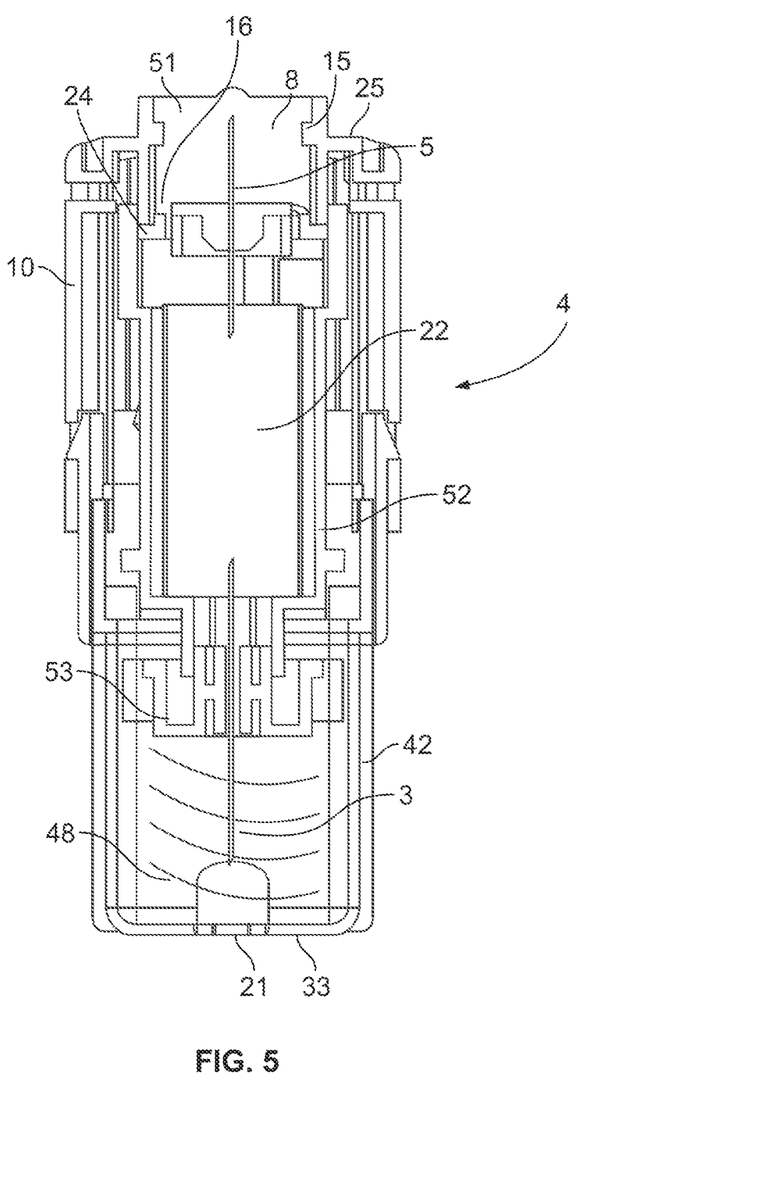
FIG. 5 is a sectional view of one embodiment of the medicated module of our invention.
Figure 6A:
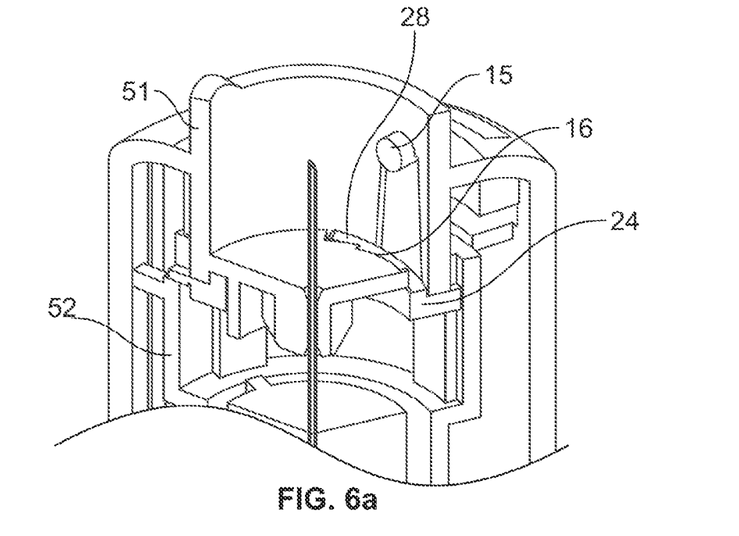
FIG. 6a illustrates a sectional perspective view of the proximal end of the medicated module of FIG. 5 showing the locking plate position prior to attachment of the drug delivery device.
Figure 6B:
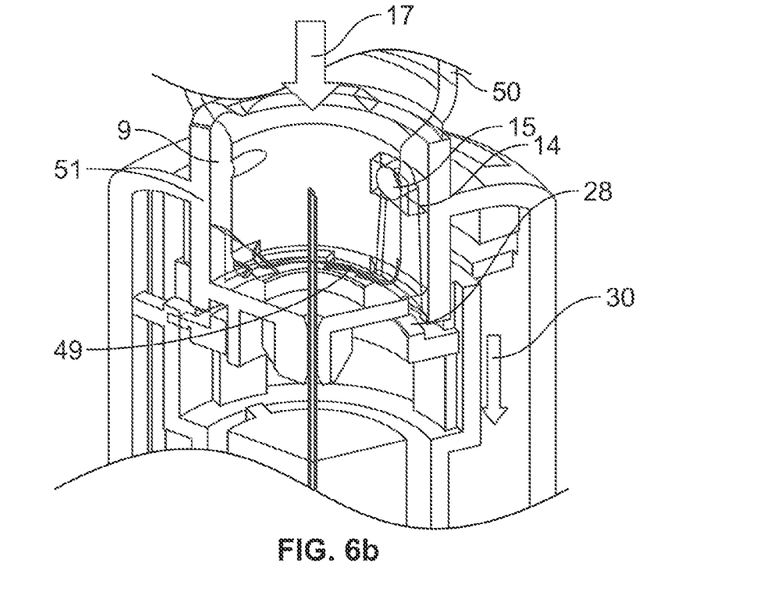
FIG. 6b illustrates a sectional perspective view of the proximal end of the medicated module of FIG. 5 showing the locking plate position after attachment of the drug delivery device.

FIGS. 5, 6a, and 6b illustrate the upper hub 51 of the medicated module 4 with a corresponding radial protrusion 15 that engages slot 14 on the engagement means 9 of cartridge holder 50. The embodiment shown in FIG. 5 has the benefit of the second medicament as a single dose being contained entirely within reservoir 22, hence minimizing the risk of material incompatibility between the second medicament and the materials used in the construction of the medicated module 4, specifically housing 10, bypass housing 52, or any of the other parts used in the construction of the medicated module.

Figure 9:
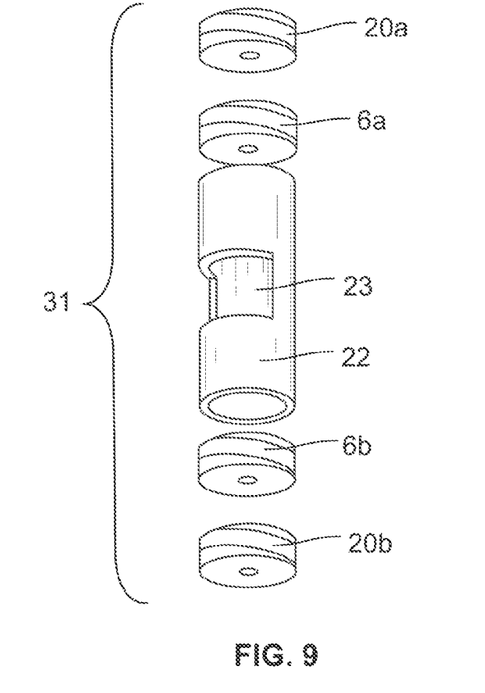
FIG. 9 is an exploded view of the capsule or reservoir containing the second medicament.
Figure 10:
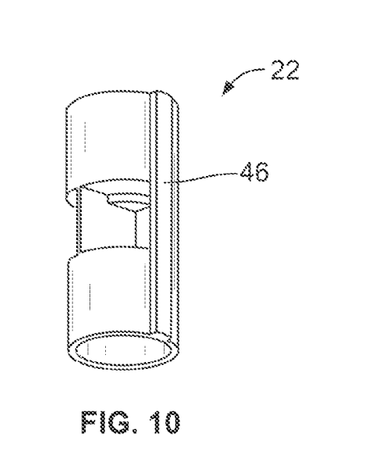
FIG. 10 is a perspective view of the reservoir showing part of the bypass.
Figure 11:
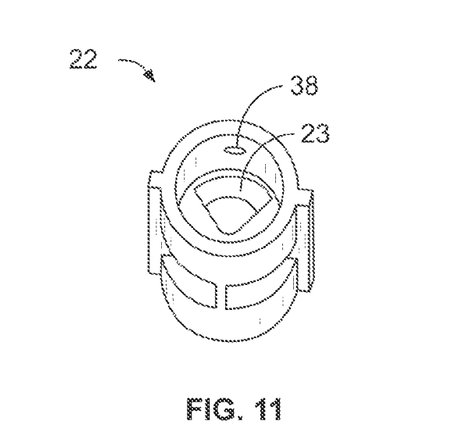
FIG. 11 is another perspective view of the reservoir showing the flow distributor.

To minimize the residual volume of the second medicament, caused by recirculation and/or stagnant zones, that might remain in capsule 31 at the end of the dispense operation, it is preferable to have a flow distributor 23 as an integral part of reservoir 22 (see FIGS. 9,10 and 11). The reservoir 22 containing the single dose of the secondary medicament can be sealed with septa 6a and 6b, which are fixed to the capsule using keepers or plugs 20a and 20b. Preferably the keepers have fluid channels that are in fluid communication with needles 3 and 5 and with bypass 46, which is preferably part of the inside surface of bypass housing 52. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 should ensure that at least about 80% of the second medicament is expelled from reservoir 22 through the distal end of needle 3. Most preferably at least about 90% should be expelled. Ideally, displacement of the first medicament in a primary reservoir (not shown) contained in cartridge holder 50 and through the capsule 31 will displace the single dose of the second medicament stored in reservoir 22 without substantial mixing of the two medicaments.

Prior to attachment of medicated module 4 to cartridge holder 50 of the drug delivery device 7, locking plate 24 is in the first locked position such that engagement ramps 28 (see FIG. 3) are exposed in cutout 16 (see FIGS. 5, 6a and 6b). Upper hub contact face 40 on the locking plate engages a corresponding face on the cutout of upper hub 51 and prevents locking plate 24 from rotating. Locking plate slots 18 are engaged with locking plate engagement ribs 35 such that the locking plate is rotationally fixed to the bypass housing 52. In this first locked position, any attempt to rotate the bypass housing will fail because the locking plate is fixed to the upper hub through the hub contact face 40. Additionally, axial detent tabs 44 are engaged with detent engagement faces 34 on bypass housing 52 to prevent distal movement of the locking plate 24, which would disengage hub contact face 40 from the cutout 16 in the upper hub.

Attachment of the medicated module 4 to the multi-use device 7 causes the locking plate 24 to move to its second position or triggering state. As cartridge holder 50 is inserted into upper hub 51, tab 49 on attachment means 9 engages ramp 28 on the proximal or upper side of locking plate 24 causing the plate to be pushed down axially in the distal direction. As the slot 14 engages radial protrusion 15 and rotates to complete the attachment, tab 49 moves along the bearing surface on ramp 28. Preferably more than one ramp and tab combination is used. The ramps are configured with increasing height such that as the tab 49 moves along the length of the ramp the plate moves axially in the distal direction until the hub contact face disengages with the cutout 16. Once disengaged, the locking plate can then rotate relative to upper hub 51. The distal movement of the locking plate also causes the axial detent tabs 44 to deform, further allowing the locking plate to move distally. Once in the triggering state, there is nothing to prevent the bypass housing from rotating and moving proximally.

Figure 7:
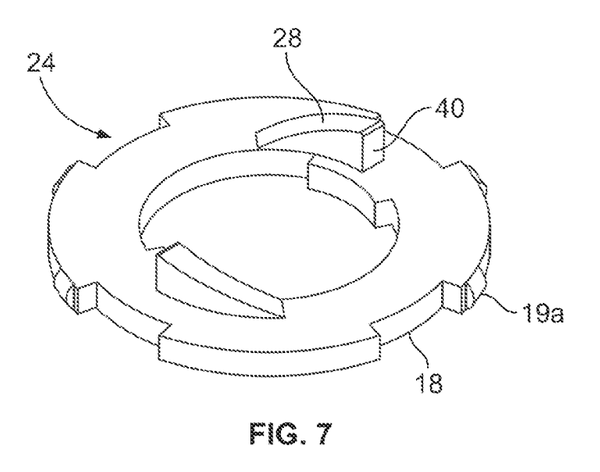
FIG. 7 illustrates a perspective view of another embodiment of the locking plate of our invention.
Figure 8:
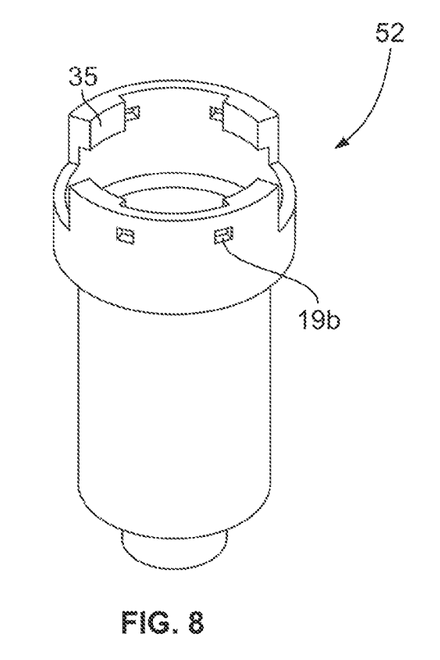
FIG. 8 illustrates a perspective view of another embodiment of the bypass housing configured to work with the locking plate illustrated in FIG. 7.

An alternate locking plate and bypass housing design is shown in FIGS. 7 and 8. In this design the locking plate 24 is configured with steeper ramps 28 such that the tab 49 on the cartridge holder pushes the locking plate down in the distal direction to disengage locking plate slots 18 from bypass ribs 35, thus allowing the bypass housing 52 to rotate relative to the locking plate and relative to the upper hub. Snap fasteners 19a and 19b work in a similar fashion to detent engagement face 34 and axial detent tabs of the embodiment shown in FIG. 3.

The attachment of the cartridge holder 50 to the medicate module 4 also causes needle 5 to penetrate a septum (not shown) sealing the distal end of the cartridge of primary medicament (not shown) positioned in cartridge holder 50 of the multi-use device 7. Once needle 5 has passed through the septum of the cartridge, fluid connection is made between the first medicament and the needle 5. At this point, the system can be primed by dialing out a small number of units (or cocking the device if only a single dose selection is possible) using dose dial sleeve 62. Once the device 7 is primed, activation of the needle guard 42 allows dispense of the medicaments by subcutaneously injecting the medicaments via activation of a dose button 13 on device 7. The dose button of our invention can be any triggering mechanism that causes the dose of the first medicament that was set by the dose dial sleeve 62 to move towards the distal end 32 of the device. In a preferred embodiment the dose button is operably connected to a spindle that engages a piston in the primary reservoir of the first medicament. In a further embodiment the spindle is a rotatable piston rod comprising two distinct threads.

Figure 3:
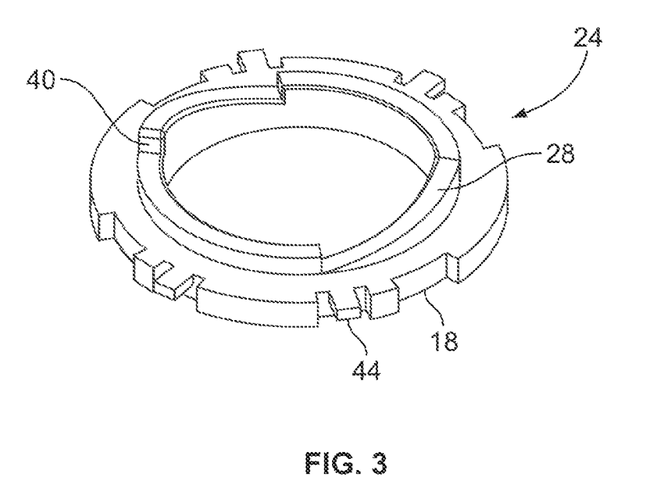
FIG. 3 illustrates a perspective view of one embodiment of the locking plate of our invention.
Figure 4:
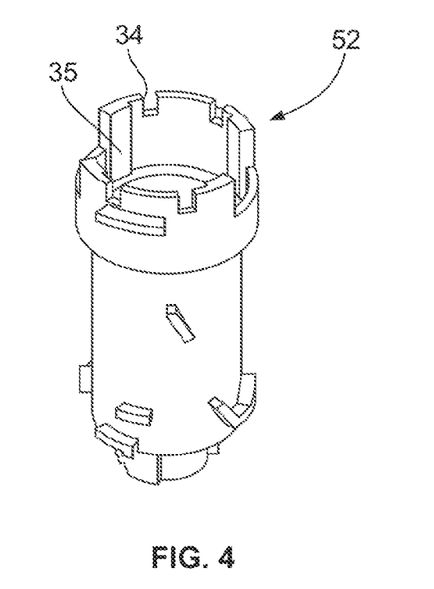
FIG. 4 illustrates a perspective view of one embodiment of the bypass housing configured to work with the locking plate illustrated in FIG. 3.

One embodiment of the medicated module 4 of our invention is illustrated in FIGS. 2, 3 and 4. In these embodiments the medicated module 4 contains a capsule 31 comprising a reservoir 22, two keepers 20a and 20b, and two seals 6a and 6b. Reservoir 22 contains a fixed single dose of a secondary medicament. In some cases this secondary medicament may be a mixture of two or more drug agents that can be the same or different from the primary drug compound in the drug delivery device 7. Preferably the capsule is permanently fixed within the medicated module, however, in some cases it may be preferred to design the module such that the capsule can be removed when empty and replaced with a new capsule.

In the embodiments shown in FIGS. 4 and 10, capsule 31 has ends that are sealed with pierceable membranes or septa 6a and 6b that provide a hermetically sealed and sterile reservoir 22 for the second medicament. A primary or proximal engagement needle 5 can be fixed in hub 51 connected to the proximal end of housing 10 of the module and configured to engage capsule 31 at some predetermined axial travel of the needle guard moving in the proximal direction during injection. The outlet, or distal needle 3, is preferably mounted in lower hub 53 and initially protrudes into lower keeper 20b. The proximal end of needle 3 pierces the lower septum 6b as the lower hub is pushed by biasing member 48 in the proximal direction as the needle guard 42 is retracted a predetermined distance into outer housing 10 during injection.

As mentioned, before attachment to the drug delivery device the module is in a locked state. This can be evident from window 54 that contains indicia illustrating the locked state. When attached to the delivery device, the locking plate moves to the triggering state and this can also be shown in window 54. And finally, after the module has been used a third indicia can be viewed through window 54. Preferably, the indicia appear on an indicator 41 that shows through window 54 to inform the user of the three possible states of the medicated module. The indicator is preferably a color stripe or band on the outer surface of one of the various parts of the medicated module visible through an aperture 54 in the outer body. One color could designate the locked state, another color the triggering state or prime state of the module and a third color would indicate that the module is in finished or locked state. Additionally, another color could be used to denote the transition through the trigger or "commit" point in case a user stops injection after trigger point but before "commit" point. For example, a yellow color could indicate the locked state, a green color could indicate the triggering state and a band of red color could be used to indicate that the module has been used and is locked. An orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that the needle guard is made form a transparent material.

The needle guard 42 is slidably engaged with the inner surface of outer housing 10, preferably by engagement of one or more ribs 27 and channels (not shown) on the inside surface the outer housing. Of course, the rib and channel can be reversed where the channels are located on the outside surface of needle guard 42. Preferably, retention snaps (not shown) prevent the guard from disengaging the outer housing at its fully extended position. A portion of the proximal end of housing 10 defines an upper hub 51 that holds needle 5. Optionally, as illustrated in FIG. 5, a shoulder cap 25 may be added to the proximal outer surface of outer housing 10. This shoulder cap can be configured to serve as indicia to identify to a user the type/strength of medicament contained in the module. The indicia can be tactile, textual, color, taste or smell.

The compression spring 48 is positioned between the distal end of lower hub 53 and the inner proximal face of guard 42 to bias the guard 42 into an extended (guarded) position as illustrated in FIG. 5. Upon assembly, the proximal end of spring 48 positioned against lower hub 53, which is prevented from moving axially in the proximal direction by locking plate 24. As the needle guard 42 is pushed against an injection site it retracts proximally up into the outer housing 10, but is constrained from rotating by engagement of the ribs and channels. Preferably, the axial movement of the needle guard in the proximal direction causes the lower hub and bypass housing to also move proximally as the locking plate is not longer preventing the bypass housing from rotating. The engagement and configuration of the reservoir 22 with the lower hub 53 is selected to allow the lower hub to move a greater proximal distance than the reservoir so as to allow the proximal end of needle 3 to come into fluid communication with the second medicament.

One possible feature of our medicated module assembly is the inclusion of user feedback that is given when the assembly is used. In particular, the assembly could emit an audible and/or tactile "click" to indicate to the user that they have firstly triggered the device and secondly reached a "commit" point such that the needle guard will lock safely out upon completion of the injection/removal of the guard from the injection site.

As mentioned, the distal end of the guard 42 has a planar surface 33 that provides an added measure of safety and reduces the pressure exerted by the guard on the injection site during an injection with our needle assembly. Because the planar surface 33 substantially covers access to needle 3 a user is prevented from gaining access to the distal tip of the needle after the assembly is in the locked position. Preferably, the diameter of needle pass through hole 21 in the planar surface is no more than 10 times that of the outer diameter of needle cannula 3.

In any of the above described embodiments of our invention the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

To minimize diffusion of the secondary medicament contained in the capsule within the medicated module into the primary medicament during dispense of the medicaments the reservoir 22 has an integral flow distributor 23. This flow distributor also ensures efficient expulsion of the second medicament from the system and greatly minimizes residual volume. One possible embodiment of the reservoir 22 and flow distributor 23 is illustrated in FIGS. 9-11. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable, for example material like COC and COP.

The flow distributor 23 is configured and positioned in reservoir 22 such that the secondary medicament fills flow channels that are defined by the shape and location of one or more channels (not shown) inside the reservoir. The shape of the flow channels can be optimized for a plug flow of medicament by varying the dimensions of the flow distributor and/or channels. The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module comprising:
an outer housing including an upper hub having a first needle configured for attachment to a drug delivery device;
a bypass housing inside the outer housing adapted to rotate and move proximally relative to the outer housing, the bypass housing including a reservoir containing a medicament,
a locking plate slidably coupled to the bypass housing and movable between a locked state prior to attachment of the drug delivery device to the upper hub and a triggerable state after attachment of the drug delivery device to the upper hub,
wherein, when in the locked state, the locking plate engages the upper hub and prevents the bypass housing from rotating relative to the upper hub, and
wherein, when in the triggerable state, the locking plate disengages the upper hub and the bypass housing is rotatable from a first angular position to a second angular position relative to the outer housing, wherein in the second angular position, the bypass housing translates axially relative to the outer housing and the reservoir is in fluid communication with the first needle.

2. A medicated module according to claim 1, wherein the bypass housing has a lower hub with a second needle located at the distal end of the bypass housing.

3. A medicated module according to claim 2, wherein a needle guard is coupled to the outer housing free to move axially, between defined constraints, within the outer housing and restrained rotationally with regard to the outer housing, wherein in an extended position, the needle guard covers the second needle.

4. A drug delivery system to deliver two or more medicaments operable through a single dispense interface, comprising,
   a primary reservoir of medicament containing at least one drug agent;
   a dose button operably connected to the primary reservoir of medicament;
   a single dispense interface configured for fluid communication with the primary reservoir; and
   the medicated module of claim 1.

5. A drug delivery system to deliver two or more medicaments operable through a single dispense interface, comprising a drug delivery device and a medicated module of claim 1, the drug delivery device comprising a primary reservoir of medicament containing at least one drug agent; and a dose button operably connected to the primary reservoir of medicament.

6. A drug delivery system according to claim 5, wherein when the medicated module is attached to the drug delivery device fluid communication is made between the medicament in the primary reservoir and the first needle.

7. A drug delivery system according to claim 5, wherein when the medicated module is attached to the drug delivery device the locking plate is disengaged from the upper hub and axial movement of the needle guard compresses a biasing member exerting a force in the proximal direction on the lower hub and the bypass housing urging them both to move proximally, causing the needle cannula in the upper and lower hubs to become fluidly engaged with the medicament in the reservoir.

8. A drug delivery system according to claim 5, wherein the drug delivery device comprises at least one projection configured to engage the locking plate through the cutout.

9. A drug delivery system according to claim 8, wherein the at least one projection of the drug delivery device engages with a bearing surface of the locking plate causing the locking plate to be axially disengaged from the bypass housing and to be moved axially in distal direction allowing the locking plate to rotate relative to the upper hub.

10. A medicated module attachable to a drug delivery device, comprising,
   a) an outer housing having a proximal end, a distal end, and an inner surface, where the proximal end has an upper hub and a connector configured for attachment to a drug delivery device;
   b) a bypass housing inside the outer housing;
   c) a locking plate positioned between the proximal end of the bypass housing and the distal end of the upper hub wherein the locking plate is rotationally fixed to the bypass housing;
   d) a reservoir within the bypass housing comprising a medicament;
   e) a needle guard having inner and outer walls, where the inner wall engages the bypass housing to cause rotation of the bypass housing when the guard is moved axially, and where the outer wall is slidably engaged with the inner surface of the outer housing;
   f) a lower hub located at the distal end of the bypass housing; wherein the lower hub contains a double-ended needle cannula and
   g) a biasing member engaged between the needle guard and the lower hub,
   wherein the upper hub has a cutout that exposes a portion of the locking plate, wherein
   in a first position, the locking plate is in engagement with the upper hub and rotation of the bypass housing is prevented; and wherein
   in a second position, the locking plate is disengaged from the upper hub and the bypass housing is allowed to rotate relative to the outer housing.

11. The medicated module of claim 10, where the locking plate has a proximally projecting bearing surface exposed through the cutout.

12. The medicated module of claim 10, where the locking plate has a locking slot configured to engage with ribs on the bypass housing such that the locking plate is rotationally fixed to the bypass housing.

13. The medicated module of claim 10, where the locking plate has axial detent tabs configured to engage with detent engagement faces on the bypass housing to prevent distal movement of the locking plate.

14. The medicated module of claim 10, where the locking plate is engaged to the bypass housing through snap fasteners to prevent distal movement of the locking plate.

15. The medicated module of claim 10 where the locking plate has an outer housing contact face.

16. The medicated module of claim 15, where the locking plate has a first locked position wherein the outer housing contact face is engaged with the upper hub to prevent rotation of the bypass housing and a second unlocked position, wherein the outer housing contact face is disengaged from the upper hub to allow the bypass housing to rotate and move proximally.

17. The medicated module of claim 10, where the upper hub holds a double-ended needle cannula.

18. The medicated module of claim 10, wherein the biasing member is a compressed spring that exerts a force on the lower hub and the bypass housing.

19. The medicated module of claim 10, where the reservoir is a single molded component having an internal cavity with an integral flow distributor.

20. The medicated module of claim 10, where the reservoir contains a liquid medicament.

21. The medicated module of claim 10, where the medicament in the reservoir comprises a GLP-1.

22. The medicated module of claim 10 where the medicament in the reservoir comprises a premix of insulin and a GLP-1.

23. The medicated module of claim 10, wherein the locking plate has a locked state, where the locking plate constrains the bypass housing to the upper hub of the outer housing, and a triggerable state, wherein the locking plate has been moved axially and is no longer locked to the outer housing thereby allowing rotation of the bypass housing.

24. The medicated module of claim 10, wherein when the medicated module is attached to a drug delivery device, the locking plate is in the second position.

25. A drug delivery device comprising at least one projection configured to engage the locking plate through the cutout of the medicated module of claim 10.

* * * * *